(12) United States Patent
Chang et al.

(10) Patent No.: US 8,734,723 B2
(45) Date of Patent: May 27, 2014

(54) LIQUID CRYSTAL GAS SENSOR CELL AND THE USE THEREOF

(71) Applicant: Industrial Technology Research Institute, Hsinchu (TW)

(72) Inventors: Chin-Kai Chang, Tainan (TW); Hui-Lung Kuo, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/014,365

(22) Filed: Aug. 30, 2013

(65) Prior Publication Data

US 2014/0004004 A1   Jan. 2, 2014

Related U.S. Application Data

(62) Division of application No. 13/347,710, filed on Jan. 11, 2012.

(30) Foreign Application Priority Data

Sep. 26, 2011   (TW) .............................. 100134593 A

(51) Int. Cl.
*G01J 1/48* (2006.01)

(52) U.S. Cl.
USPC ............ 422/86; 422/83; 422/85; 422/88; 422/90; 422/91; 422/98; 435/807; 436/113; 436/118; 436/121; 436/131; 436/144; 436/149; 436/151; 436/153; 436/161; 436/172

(58) Field of Classification Search
USPC ........ 422/86, 83, 85, 88, 90, 91, 98; 349/175; 436/113, 118, 121, 131, 144, 149, 151, 436/153, 161, 172; 435/807
See application file for complete search history.

(56) References Cited

U.S. PATENT DOCUMENTS

| | | | |
|---|---|---|---|
| 5,615,031 A * | 3/1997 | Saiuchi et al. | ................ 349/149 |
| 5,634,426 A | 6/1997 | Tomlinson et al. | |
| 6,137,576 A | 10/2000 | Pauluth et al. | |
| 6,423,272 B1 | 7/2002 | Boden et al. | |
| 7,545,557 B2 | 6/2009 | Iftime et al. | |
| 7,576,829 B2 | 8/2009 | Kikuchi et al. | |
| 2001/0052961 A1 * | 12/2001 | Towler et al. | ................ 349/177 |
| 2010/0072065 A1 | 3/2010 | Naito et al. | |
| 2010/0170795 A1 | 7/2010 | Cowburn et al. | |

FOREIGN PATENT DOCUMENTS

| | | |
|---|---|---|
| CN | 1934224 | 3/2007 |
| CN | 201765209 U | 3/2011 |
| TW | 200424291 | 11/2004 |
| TW | 201031899 | 9/2010 |

OTHER PUBLICATIONS

"Office Action of U.S. Appl. No. 13/347,710" issued on Feb. 4, 2013, p. 1-p. 11.
"Final Office Action of U.S. Appl. No. 13/347,710" issued on May 31, 2013, p. 1-p. 7.
"Office Action of Taiwan counterpart application" issued on Oct. 9, 2013, p. 1-p. 5.

* cited by examiner

*Primary Examiner* — Dennis M White
(74) *Attorney, Agent, or Firm* — Jianq Chyun IP Office

(57) ABSTRACT

A gas sensor cell using a liquid crystal composite material is provided. The gas sensor cell has recovery capability and can be reused. Upon gas adsorption, the liquid crystal composite material has visually detectable color changes and changes in electrical properties to facilitate the measurement of gas concentration from low to high.

10 Claims, 4 Drawing Sheets
(3 of 4 Drawing Sheet(s) Filed in Color)

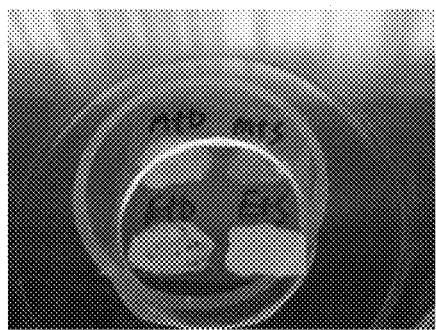 
FIG. 3A  FIG. 3B
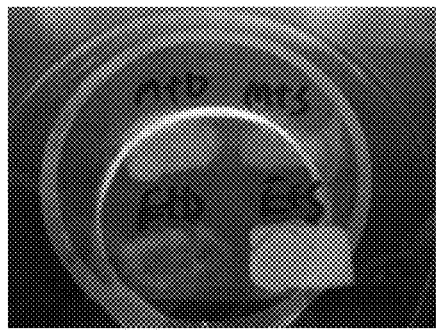 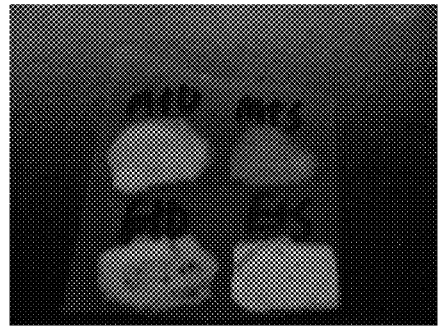
FIG. 3C  FIG. 3D

LIQUID CRYSTAL GAS SENSOR CELL AND THE USE THEREOF

CROSS-REFERENCE TO RELATED APPLICATION

This application is a divisional application of and claims the priority benefit of U.S. application Ser. No. 13/347,710, filed on Jan. 11, 2012, now pending, which claims the priority benefit of Taiwan application serial no. 100134593, filed on Sep. 26, 2011. The entirety of each of the above-mentioned patent applications is hereby incorporated by reference herein and made a part of specification.

BACKGROUND OF THE INVENTION

1. Technical Field

The disclosure relates to a sensor. More particularly, the disclosure relates to a liquid crystal gas sensor cell applied for sensing gases.

2. Background

An electronic gas sensor can sense gases and detect compositional changes in the sensed gas by way of electrical signals. Since the process of manufacturing the electronic gas sensor is complicated, and additional electronic instruments are often required, the costs of the electronic gas sensor are rather significant. Moreover, sensing materials used in the normal electronic gas sensor often operate under high sensing temperature, which drastically restrains the actual use of the electronic gas sensor.

By contrast, an optical gas sensor can sense gas and detect changes of the sensed gas by way of optical signals. However, the optical gas sensor, in most cases, is not working at low sensitivity and over wide measurement range.

SUMMARY OF THE INVENTION

The disclosure is directed to a gas sensing method. According to the method, various types of gas molecules can be simultaneously sensed or detected through changes in optical and/or electrical signals of at least one sensing material. The sensing material at least includes a cholesteric liquid crystal material and a conductive substance. Upon gas adsorption, the sensing material not only has visually detectable color changes (i.e., changes in optical signals) but also varies in electrical properties.

In an exemplary embodiment of the disclosure, a liquid crystal composite material at least including a cholesteric liquid crystal material and at least one conductive substance is provided. The liquid crystal composite material is characterized by having color changes and changes in electrical properties upon gas adsorption. The cholesteric liquid crystal material includes at least one chiral dopant and one or more biphenyl compound liquid crystal molecules. Besides, the biphenyl compound liquid crystal molecules may be represented by a general formula (I) below:

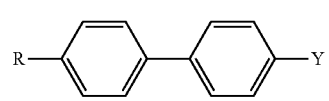

(I)

Here, Y respectively denotes halide (including F or Cl) or cyano (—C≡N), and R represents alkyl, alkyloxy, phenylalkyl, alkenyl, or alkenyloxy.

According to an exemplary embodiment of the disclosure, the conductive substance is selected from carbon black, carbon nanotubes, metal micro-particles, metal oxide micro-particles, or micro-particles having conductive layers thereon.

According to an exemplary embodiment of the disclosure, the chiral dopant is selected from dioctan-2-yl biphenyl-4,4'-dicarboxylate, benzoic acid, 4-(trans-4-pentylcyclohexyl)-,1, 1'-[(1S)-1-phenyl-1,2-ethanediyl]ester, or isopentylcyanobiphenyl.

According to an exemplary embodiment of the disclosure, resistance of the liquid crystal composite material decreases upon gas adsorption, and the resistance of the liquid crystal composite material ranges from 100 MΩ to 0.001 MΩ.

According to an exemplary embodiment of the disclosure, a color spectrum of the liquid crystal composite material ranges from a wavelength of ultraviolet light to a wavelength of near-infrared light.

In an exemplary embodiment of the disclosure, a gas sensor cell at least including a substrate, an electrode layer, a liquid crystal composite material layer, and a signal collecting and displaying unit is provided. The electrode layer is located on the substrate. The liquid crystal composite material layer covers the electrode layer and the substrate. The signal collecting and displaying unit is electrically connected to the electrode layer.

According to an exemplary embodiment of the disclosure, the electrode layer is made of a silver conductive paste. The substrate is a transparent plastic substrate or a glass substrate. The liquid crystal composite material includes a halide or cyano biphenyl compound liquid crystal material, a chiral dopant, and carbon nanotubes.

According to an exemplary embodiment of the disclosure, the signal collecting and displaying unit is an optical signal collecting and displaying device or an electrical signal collecting and displaying device, and the signal collecting and displaying unit further includes an optical or electrical signal analyzing unit.

Several exemplary embodiments accompanied with figures are described in detail below to further describe the disclosure in details.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 3A to FIG. 3D show color changes of four cholesteric liquid crystal material samples upon methanol detected by the four cholesteric liquid crystal material samples.

DETAILED DESCRIPTION OF DISCLOSED EXEMPLARY EMBODIMENTS

Figure 1:
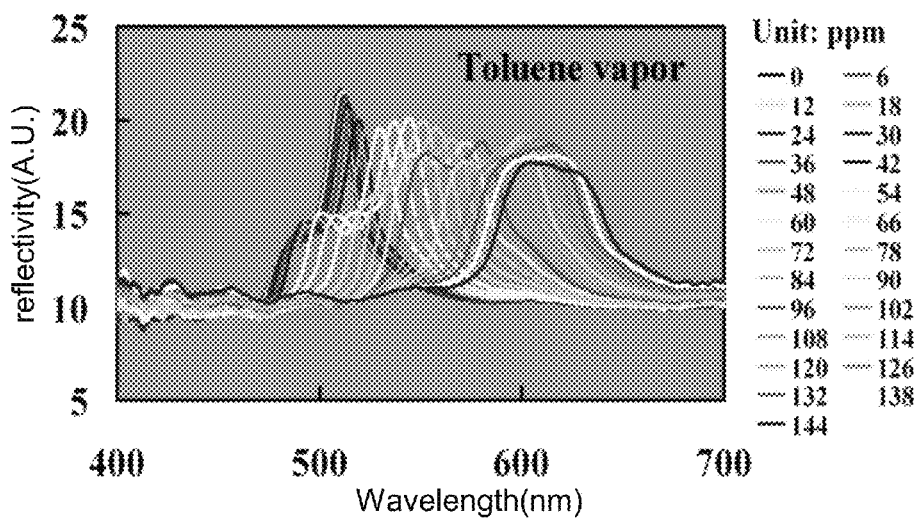
FIG. 1 is a graph showing changes in reflective wavelengths when a cholesteric liquid crystal material adsorbs toluene vapor of different concentrations.

The disclosure relates to use of a liquid crystal composite material for sensing gas. The liquid crystal composite material includes at least one or more cholesteric liquid crystal materials and at least one or more conductive substances. The cholesteric liquid crystal material includes at least one chiral dopant. Here, the liquid crystal composite material is characterized in that the liquid crystal composite material may simultaneously have visually detectable color changes (i.e. detectable to the naked-eye) and changes in electrical properties upon gas adsorption.

The cholesteric liquid crystal may be pure cholesteric liquid crystal having no additives, nematic liquid crystal containing chiral dopants, or nematic liquid crystal containing cholesteric liquid crystal molecules. Generally, the nematic liquid crystal containing chiral dopants is preferably used herein. Through the combinations of different types of nematic liquid crystals and different chiral dopants, various types of cholesteric liquid crystal materials which are diverse in the thermal, optical, and electrical properties can be obtained. Hence, based on actual requirements, the cholesteric liquid crystal materials with different reflective wavelengths, ranges of liquid crystal phases, and photoelectric properties may be made. After the chiral dopant is added to the nematic liquid crystal, the liquid crystal material then has a spiral structure. A pitch (P) refers to a normal distance over which the liquid crystal molecules undergo a 360-degree twist (2π). The pitch P is determined based on the type of the chiral dopant, the amount of additives, or the temperature.

In the disclosure, the cholesteric liquid crystal material of the liquid crystal composite material is the nematic liquid crystal containing the chiral dopants.

Specifically, the cholesteric liquid crystal material of the liquid crystal composite material in this disclosure may include one or more biphenyl compound liquid crystal molecules, and the biphenyl compound liquid crystal molecules can be represented by the following general formula (I):

Here, Y respectively denotes halide (including fluoro —F or chloro —Cl) or cyano (—C≡N), and R represents alkyl, alkyloxy, phenylalkyl, alkenyl, or alkenyloxy.

For instance, the cholesteric liquid crystal material can be a mixture of various types of aliphatic long-chain cyanobiphenyl compound liquid crystal molecules with a trade name E7 (obtained from Merck). Alternatively, the cholesteric liquid crystal material may be fluoro biphenyl compound liquid crystal molecules with a trade name OCB (optically compensated bend, MJ01744 obtained from Merck).

The chiral dopant included in the cholesteric liquid crystal material may be Benzoic acid, 4-(trans-4-pentylcyclohexyl)-, 1,1'-[(1S)-1-phenyl-1,2-ethanediyl]ester with a trade name S1011 (obtained from Merck), dioctan-2-yl biphenyl-4,4'-dicarboxylate with a trade name DBD (obtained from Merck), or isopentylcyanobiphenyl with a trade name CB15 (obtained from Merck).

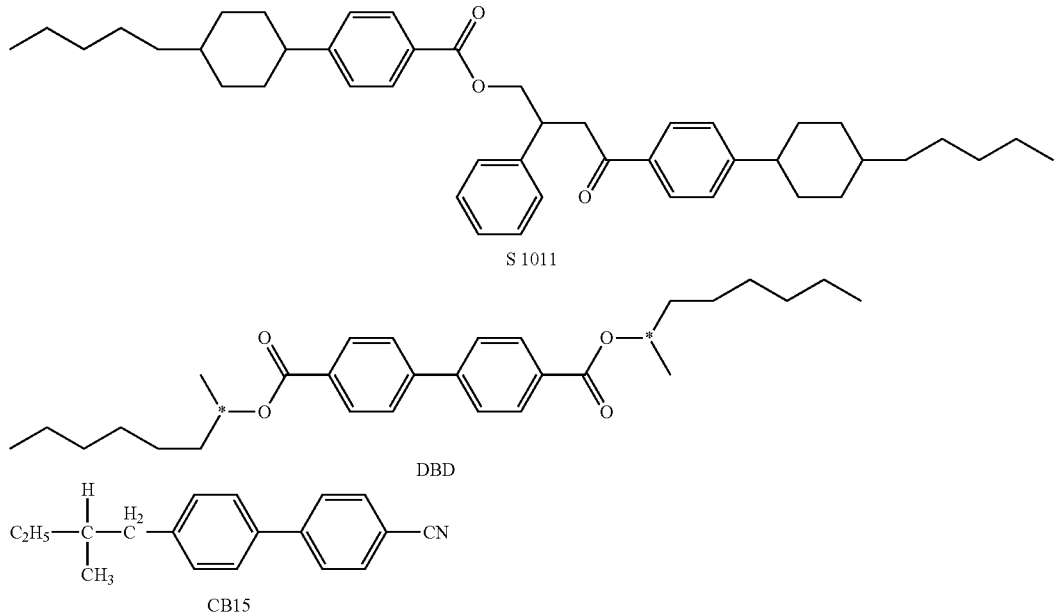

In the disclosure, the cholesteric liquid crystal material of the liquid crystal composite material is a nematic liquid crystal material containing the chiral dopant. The cholesteric liquid crystal material has an initial alignment, which is changed upon gas adsorption. Additionally, different concentrations of the adsorbed gas result in the variations of reflective wavelengths of the cholesteric liquid crystal material. Based on said principle, one single cholesteric liquid crystal material can be used to sense whether a specific gas exists or not or to detect the amount of the specific gas. Moreover, different types of liquid crystals can be applied in cooperation with different chiral dopants in order to detect a variety of gases.

Figure 2:
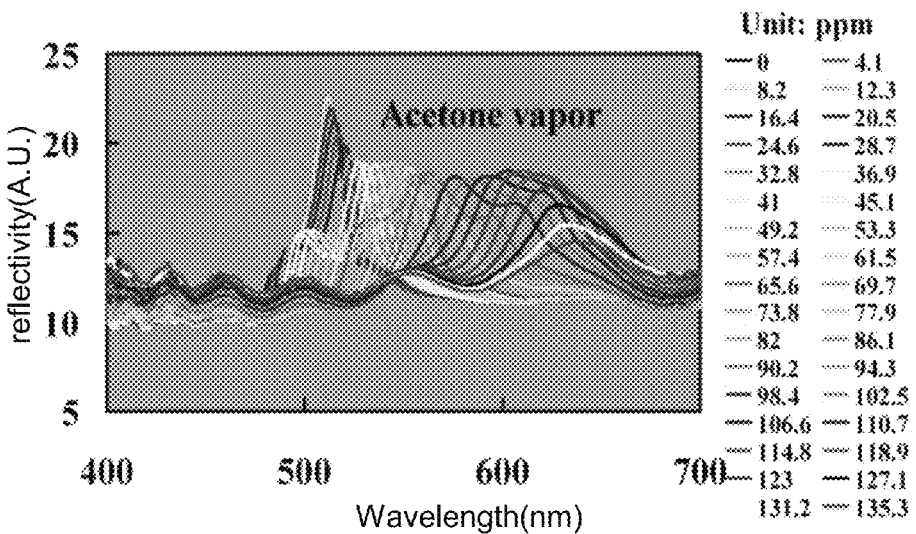
FIG. 2 is a graph showing changes in reflective wavelengths when a cholesteric liquid crystal material adsorbs acetone vapor of different concentrations.

FIG. 1 is a graph showing changes in reflective wavelengths when a cholesteric liquid crystal material (E7/S1011/DBD) adsorbs toluene vapor of different concentrations. Here, the vertical axis refers to relative reflectivity. FIG. 2 is a graph showing changes in reflective wavelengths when a cholesteric liquid crystal material (E7/S1011/DBD) adsorbs acetone vapor of different concentrations. Here, the vertical axis refers to relative reflectivity. As indicated in FIG. 1 or FIG. 2, the greater the concentration of adsorbed gas, the longer the reflective wavelength of liquid crystal (the reflective wavelength of the liquid crystal shifting from visible light to infrared light), and the lower the relative reflectivity. Hence, when the liquid crystal composite material of this disclosure is applied to detect the gas of a relatively low concentration, it is not necessary to add any conductive substance. Instead, after adsorbing the gas of a relatively low concentration, the pitch of the cholesteric liquid crystal material is altered, which leads to color changes (i.e. changes of the reflective wavelength). Thereby, whether the gas (the adsorbed gas) is sensed can be determined, or the concentration of the adsorbed gas can be determined based on the color changes (changes in the reflective wavelength).

By contract, when the gas of a relatively high concentration is to be sensed, the conductive substance may be used in conjunction because the range of the reflective wavelength may exceed the wavelength range of visible light. In this disclosure, the distribution state of the conductive particles dispersed in the liquid crystal composite material may vary upon gas adsorption. The phase changes of the cholesteric liquid crystal material caused by gas adsorption induce the conductive substance to generate a conductive network, thus resulting in changes in electrical properties. Hence, whether the gas is sensed or not may be determined through the measurement of changes in electrical properties of the liquid crystal composite material. Alternatively, the concentration of the adsorbed gas can be determined based on the changes in electrical properties of the liquid crystal composite material.

EXEMPLARY EMBODIMENTS

First Example

When the gas of a relatively low concentration is to be sensed, it is not necessary to add any conductive substance to the liquid crystal composite material. Instead, whether the gas is sensed or not can be determined based on the color changes of the reflective wavelengths generated by different cholesteric liquid crystal materials. Here, a planar substrate and an electrode layer thereon are coated with the liquid crystal materials for the measurement of electrical properties.

Specifically, two different liquid crystal (E7 and OCB) and two different chiral dopants (S1011 and DBD) are used in combinations to respectively form four different cholesteric liquid crystal material samples: C1: OCB+DBD (experiment code M+D); C2: E7+DBD (experiment code E+D); C3: OCB+S1011 (experiment code M+S); C4: E7+S1011 (experiment code E+S). Glass sheets containing the cholesteric liquid crystal material samples are respectively placed in gas tanks to observe the color changes in the cholesteric liquid crystal material samples as time goes by. Here, the concentration of the gas in the gas tank is approximately 50 ppm, and the temperature in the gas tank is around the room temperature (23° C.).

FIG. 3A to FIG. 3D show color changes of four cholesteric liquid crystal material samples upon methanol detected by the four cholesteric liquid crystal material samples. As shown in FIG. 3A to FIG. 3D, the glass sheets containing the cholesteric liquid crystal material samples are placed in gas tanks for a period of time T, 2T, 3T, and 4T, respectively. Here, the time T, 2T, 3T, and 4T is an arithmetic sequence with an equivalent time difference among one another. As shown in the drawings, the color of the sample C2 (experiment code E+D) changes with time. In the period of time 3T (shown in FIG. 3C), the color of the sample C2 changes from red into colorless after adsorbing gas. However, in the period of time 4T (shown in FIG. 3D), the color of the sample C2 turns back to red from colorless. This is because the adsorbed gas is desorbed from the sample.

As the gas adsorption process is a dynamic process and the liquid crystal samples can return to its original color or resume the original electrical properties after the gas is desorbed from the liquid crystal samples, the liquid crystal samples can be used repeatedly. Accordingly, for the gas sensor using the liquid crystal samples described in this disclosure, the gas sensor can be used many times.

Second Example

Figure 4A:
FIG. 4A to FIG. 4F show color changes of four cholesteric liquid crystal material samples upon ethanol detected by the four cholesteric liquid crystal material samples.
Figure 4B:
Figure 4C:
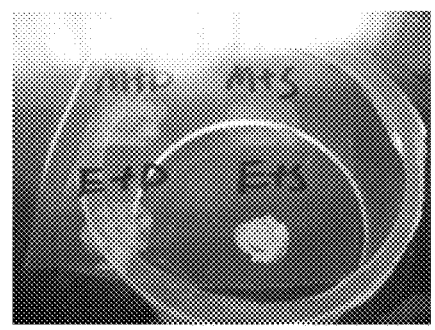
Figure 4D:
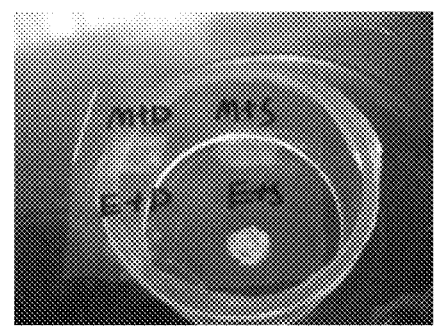
Figure 4E:
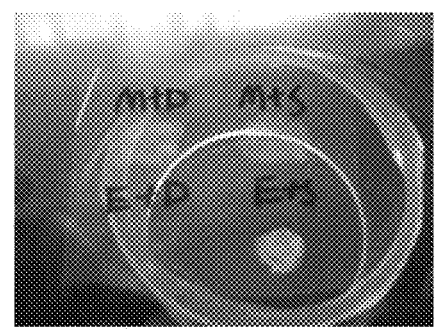
Figure 4F:
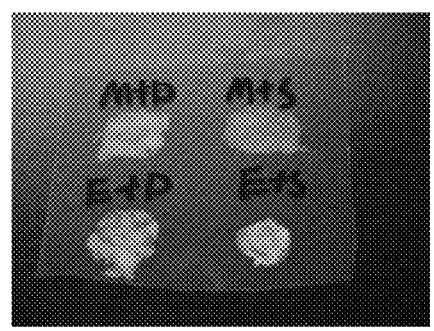

FIG. 4A to FIG. 4F show color changes of four cholesteric liquid crystal material samples upon ethanol detected by the four cholesteric liquid crystal material samples. As shown in FIG. 4A to FIG. 4F, the glass sheets containing the cholesteric liquid crystal material samples are placed in gas tanks for a period of time T, 2T, 3T, 4T, 5T, and 6T respectively. Here, the time T, 2T, 3T, 4T, 5T, and 6T is an arithmetic sequence with an equivalent time difference among one another. As shown in the drawings, the color of the sample C4 (experiment code E+S) is changed with time, and the color of the sample C4 is turned from green into red gradually. In FIG. 4F, the color of the sample C4 appears to be substantially red. By contrast, the color of the sample C2 is turned from red into colorless in the period of time 4T (as shown in FIG. 4D). However, in the period of time 6T (shown in FIG. 4F), the color of the sample C2 is turned from colorless back to red. The above-mentioned examples indicate that the gas adsorbed by the liquid crystal samples is desorbed from the samples, so that the liquid crystal samples can be repeatedly used. The above examples further exhibit that different liquid crystal samples have different gas desorption speed (i.e., the recovery speed).

Third Example

On certain experimental conditions, five common gases are detected with use of the aforesaid four cholesteric liquid crystal material samples, and the results are listed in the following Table 1.

TABLE 1

|  | Methanol | Ethanol | Toluene | n-hexane | Acetone |
|---|---|---|---|---|---|
| C1 | ★ | ★ | ★★★ | ★ | ★★★ |
| C2 | ★★★ | ★★ | ★★★★ | ★ | ★★★★★ |
| C3 | ★ | ★ | ★ | ★ | ★ |
| C4 | ★★ | ★★★ | ★★ | ★★★ | ★★★★ |

*Speed of color change (★ represents subtle color change, and ★★★★★ represents the most significant color change.)

Namely, the cholesteric liquid crystal material samples used to detect the color change speed of the following gases are described below:

Methanol: speed of color change of sample C2>speed of color change of sample C4

Ethanol: speed of color change of sample C4>speed of color change of sample C2.

Toluene: speed of color change of sample C2>speed of color change of sample C1>speed of color change of sample C4.

n-hexane: relatively significant speed of color change of sample C4.

Acetone: speed of color change of sample C2>speed of color change of sample C4>speed of color change of sample C1

When various types of gases are to be detected, different types of liquid crystal samples with different speed of color change can be applied to accurately identify a specific gas. For instance, the liquid crystal samples can be arranged in arrays, and changes in the liquid crystal samples can be observed within a certain period of time (1 represents changes; 0 represents no changes). When appropriate software (e.g., bar code design) is applied or an identification table is used in collaboration to identify the changes, it is likely to further determine whether different types of gases are detected.

By contract, when the gas of relatively high concentrations is to be sensed, one or more conductive substances may be added to the liquid crystal composite material because the range of the reflective wavelength may exceed the wavelength range of visible light. The "conductive substance" herein includes a variety of common conductive substances frequently used together with liquid crystal, such as carbon black particles, carbon nanotubes, metal (e.g., gold, silver, or copper) micro-particles, metal oxide micro-particles, or micro-particles having conductive layers thereon. Note that the common conductive substances described above should not be construed as limitations to the invention, and substitution for and adjustment of the conductive substances described herein are comprehensible to people having ordinary skill in the art and do not depart from the protection scope of the disclosure.

The cholesteric liquid crystal in the liquid crystal composite material of this disclosure is not conductive. However, after adsorbing the gas, the cholesteric liquid crystal is re-arranged (i.e., phase separation caused by gas adsorption) and the conductive substance (e.g., gold, silver, copper, carbon nanotubes, and so on) in the liquid crystal composite material is compressed and a conductive network is generated, which leads to the decrease of the resistance. Hence, whether the gas is sensed or not may be determined through measurement of changes in electrical properties. Alternatively, the concentration of the adsorbed gas can be determined based on the changes in electrical properties.

The cholesteric liquid crystal used in the experiment is E7/S1011/DBD. Carbon nanotubes (approximately 1.5% by weight) are added to the cholesteric liquid crystal, and an ultrasonic mixer is applied to well mix the carbon nanotubes and the cholesteric liquid crystal. The substrate and the electrode layer are then coated with the liquid crystal composite material (the mixture) for the measurement of electrical properties. Color of the liquid crystal composite material samples containing the carbon nanotubes is changed along with the increase in concentration of adsorbed gas (e.g., acetone). When the gas concentration is relatively low (10 ppm-200 ppm), the color of the samples is changed from green to red, and the resistance remains substantially the same; when the gas concentration is relatively high (200 ppm-1000 ppm), the color of the liquid crystal samples is changed from red to black, and the resistance is reduced from about 3 MΩ to about 0.72 MΩ.

In this disclosure, conductivity of the liquid crystal composite material gradually increases in the process of gas adsorption; during gas adsorption, and the resistance of the liquid crystal composite material ranges from 100 MΩ to 0.001 MΩ, for instance.

The visible color changes in the liquid crystal composite material in this disclosure may range from a wavelength of ultraviolet light to a wavelength of near-infrared light. For instance, the color spectrum of the liquid crystal composite material may range from a wavelength of 350 nm to a wavelength of 720 nm.

In this disclosure, a gas sensing method is provided. According to the gas sensing method, various types of gas molecules can be simultaneously sensed through changes in optical and electrical signals of the liquid crystal composite material (as the sensing material). The liquid crystal composite material characterized by photo-electrical properties (i.e., changes in optical and electrical signals at the same time) includes at least the cholesteric liquid crystal material and the conductive substance. Upon gas adsorption, the sensing material not only has visually detectable color changes but also has changes in electrical properties.

To measure the concentration of a specific gas, a linear range can be established based on the correlation between changes in electrical properties and the range of gas concentration, and a calculation formula obtained through the linear range can be applied to calculate the gas concentration according to the detected changes in electrical properties when the specific gas is actually measured.

In general, the liquid crystal composite material in this disclosure is changed in properties upon gas adsorption. In the event of lower concentrations of adsorbed gas, the liquid crystal composite material undergoes color changes; in the event of higher concentrations of adsorbed gas, the liquid crystal composite material undergoes changes in electrical properties (e.g., changes in resistance). Besides, the liquid crystal composite material of this disclosure has recovery capability; namely, after the adsorbed gas is desorbed from the liquid crystal composite material, the color and/or the electrical properties of the liquid crystal composite material return to its original state, such that the liquid crystal composite material can be used repeatedly.

The liquid crystal composite material of this disclosure can be applied to a gas sensor cell. Upon gas adsorption, the liquid crystal composite material has color changes and/or changes in electrical properties to facilitate the dynamic measurement of gas concentration over a wide range (from low to high concentrations).

Figure 5:
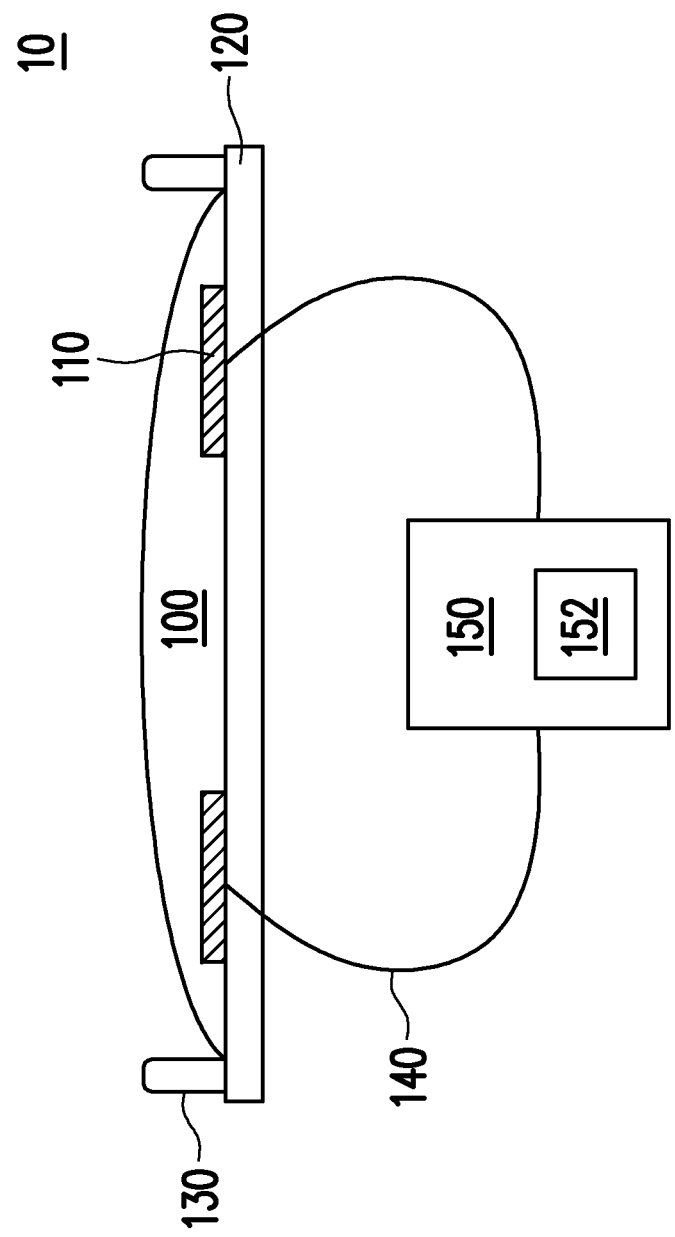
FIG. 5 is a schematic view illustrating a structure of a gas sensor cell.

FIG. 5 is a schematic view illustrating a structure of a gas sensor cell. As indicated in FIG. 5, the gas sensor cell 10 includes a substrate 120, a finger-shaped electrode layer 110 coated onto the substrate 120, and a liquid crystal composite material layer 100 coated over the finger-shaped electrode layer 110 and covering the substrate 120. The gas sensor cell 10 can further include a spacer 130 that is located on the substrate 120, surrounding the electrode layer 110 and enclosed the liquid crystal composite material layer 100. The liquid crystal composite material layer 100 is formed by coating the liquid crystal composite material described in this disclosure over the electrode layer 110 and the substrate 120. The electrode layer 110 of the gas sensor cell 10 is externally connected to a signal collecting and displaying unit 150 through a conductive wire 140, so as to form a gas sensor. The electrode layer 110 is made of a conductive silver paste, for instance, and the substrate 120 is a glass substrate or a transparent plastic substrate, for instance. According to an exemplary embodiment of the disclosure, the liquid crystal composite material includes a halide or cyano biphenyl compound liquid crystal material, a chiral dopant, and carbon nanotubes.

The signal collecting and displaying unit 150 may be an optical signal collecting and displaying device or an electrical signal collecting and displaying device. Certainly, the signal collecting and displaying unit 150 can further include an optical or electrical signal analyzing unit 152.

The gas sensor cell in the disclosure can sense gas through changes in optical and electrical signals. Besides, the gas sensor cell has recovery capability and can be reused. Upon gas adsorption, the liquid crystal composite material has naked-eye detectable color changes and changes in electrical properties to facilitate dynamic measurement of gas concentration over a wide range (from low to high concentrations).

In light of the foregoing, the liquid crystal composite material and the gas sensor cell using the liquid crystal composite material can be applied to detect or sense gases or volatile chemical compounds in the general open environment. Since the liquid crystal composite material described in this disclosure is rather sensitive and can facilitate highly dynamic measurement of wide range gas concentrations, the liquid crystal composite material may be applicable to detection of disease-related respiratory gas or inspection of trace elements in medicine.

It will be apparent to those skilled in the art that various modifications and variations can be made to the structure described in the disclosure without departing from the scope or spirit of the disclosure. In view of the foregoing, it is intended that the disclosure cover modifications and variations of this disclosure provided they fall within the scope of the following claims and their equivalents.

What is claimed is:

1. A gas sensor cell, comprising:
   a substrate;
   an electrode layer located on the substrate;
   a liquid crystal composite material layer located on the substrate and covering the electrode layer and the substrate; and
   a signal collecting and displaying unit electrically connected to the electrode layer, wherein the liquid crystal composite material layer includes at least a cholesteric liquid crystal material and at least one conductive substance mixed within the cholesteric liquid crystal material, the liquid crystal composite material being characterized by having visually detectable color changes and changes in electrical properties upon gas adsorption, the cholesteric liquid crystal material comprising at least one chiral dopant and one or more biphenyl compound liquid crystal molecules represented by a general formula (I):

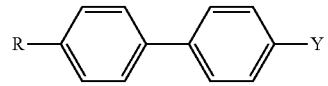

wherein Y denotes halide or cyano (—C≡N), and R represents alkyl, alkyloxy, phenylalkyl, alkenyl, or alkenyloxy.

2. The gas sensor cell as recited in claim 1, wherein the at least one conductive substance is selected from carbon black, carbon nanotubes, metal micro-particles, metal oxide micro-particles, or micro-particles having a conductive layer thereon.

3. The gas sensor cell as recited in claim 1, wherein the at least one chiral dopant is selected from dioctan-2-yl biphenyl-4,4'-dicarboxylate, benzoic acid, 4-(trans-4-pentylcyclohexyl)-,1,1'-[(1S)-1-phenyl-1,2-ethanediyl]ester, or isopentylcyanobiphenyl.

4. The gas sensor cell as recited in claim 1, wherein a resistance of the liquid crystal composite material decreases upon gas adsorption, and the resistance of the liquid crystal composite material ranges from 100 MΩ to 0.001 MΩ.

5. The gas sensor cell as recited in claim 1, wherein a color spectrum of the liquid crystal composite material ranges from a wavelength of ultraviolet light to a wavelength of near-infrared light.

6. The gas sensor cell as recited in claim 5, wherein the color spectrum of the liquid crystal composite material ranges from a wavelength of 350 nm to a wavelength of 720 nm.

7. The gas sensor cell as recited in claim 1 wherein the electrode layer is made of a conductive silver paste.

8. The gas sensor cell as recited in claim 1 wherein the substrate is a glass substrate or a transparent plastic substrate.

9. The gas sensor cell as recited in claim 1, wherein the signal collecting and displaying unit is an optical signal collecting and displaying device or an electrical signal collecting and displaying device, and the signal collecting and displaying unit further comprises an optical or electrical signal analyzing unit.

10. The gas sensor cell as recited in claim 1, further comprising a spacer located on the substrate, wherein the spacer surrounds and encloses the electrode layer and the liquid crystal composite material layer.

* * * * *